(12) United States Patent
Chowdhury et al.

(10) Patent No.: US 10,259,762 B2
(45) Date of Patent: Apr. 16, 2019

(54) METHOD OF FORMING PHENYLENE ETHER OLIGOMER

(71) Applicant: SABIC GLOBAL TECHNOLOGIES B.V., Bergen op Zoom (NL)

(72) Inventors: Rajesh Chowdhury, Bangalore (IN); Eylem Tarkin-Tas, Delmar, NY (US); Xuezhi Jin, Branford, CT (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/061,764

(22) PCT Filed: Nov. 10, 2016

(86) PCT No.: PCT/US2016/061254
§ 371 (c)(1),
(2) Date: Jun. 13, 2018

(87) PCT Pub. No.: WO2017/105682
PCT Pub. Date: Jun. 22, 2017

(65) Prior Publication Data
US 2018/0362430 A1 Dec. 20, 2018

Related U.S. Application Data

(60) Provisional application No. 62/266,749, filed on Dec. 14, 2015.

(51) Int. Cl.
*C07C 41/01* (2006.01)
*C07C 46/08* (2006.01)
(Continued)

(52) U.S. Cl.
CPC .............. *C07C 41/01* (2013.01); *C07C 37/11* (2013.01); *C07C 46/08* (2013.01); *C08G 65/44* (2013.01); *C08G 65/485* (2013.01)

(58) Field of Classification Search
CPC ......... C07C 41/01; C07C 46/08; C07C 37/11; C08G 65/485; C08G 65/44
See application file for complete search history.

(56) References Cited

U.S. PATENT DOCUMENTS 3,306,874 A 2/1967 Hay
3,306,875 A 2/1967 Hay
(Continued)

FOREIGN PATENT DOCUMENTS

EP 0550209 A2 7/1993
FR 2392055 12/1978
WO 2015102815 A1 7/2015

OTHER PUBLICATIONS

International Search Report; International Application No. PCT/US2016/061254; International Filing Date: Nov. 10, 2016; dated Jan. 19, 2017; 4 pages.
(Continued)

*Primary Examiner* — Rosalynd A Keys
(74) *Attorney, Agent, or Firm* — Cantor Colburn LLP

(57) ABSTRACT

A phenylene ether oligomer is prepared by a process that includes partially converting 2,6-dimethylphenol to 3,3',5,5'-tetramethyl-4,4'-dihydroxybiphenyl and/or 3,3',5,5'-tetramethyldiphenoquinone, converting the residual 2,6 dimethylphenol to poly(2,6-dimethyl-1,4-phenylene ether) and any 3,3',5,5'-tetramethyl-4,4'-dihydroxybiphenyl to 3,3',5,5'-tetramethyldiphenoquinone, and reacting the poly(2,6-dimethyl-1,4-phenylene ether) and 3,3',5,5'-tetramethyldiphenoquinone to form the phenylene ether oligomer. The preparation can be conducted without isolation of intermediates.

(Continued)

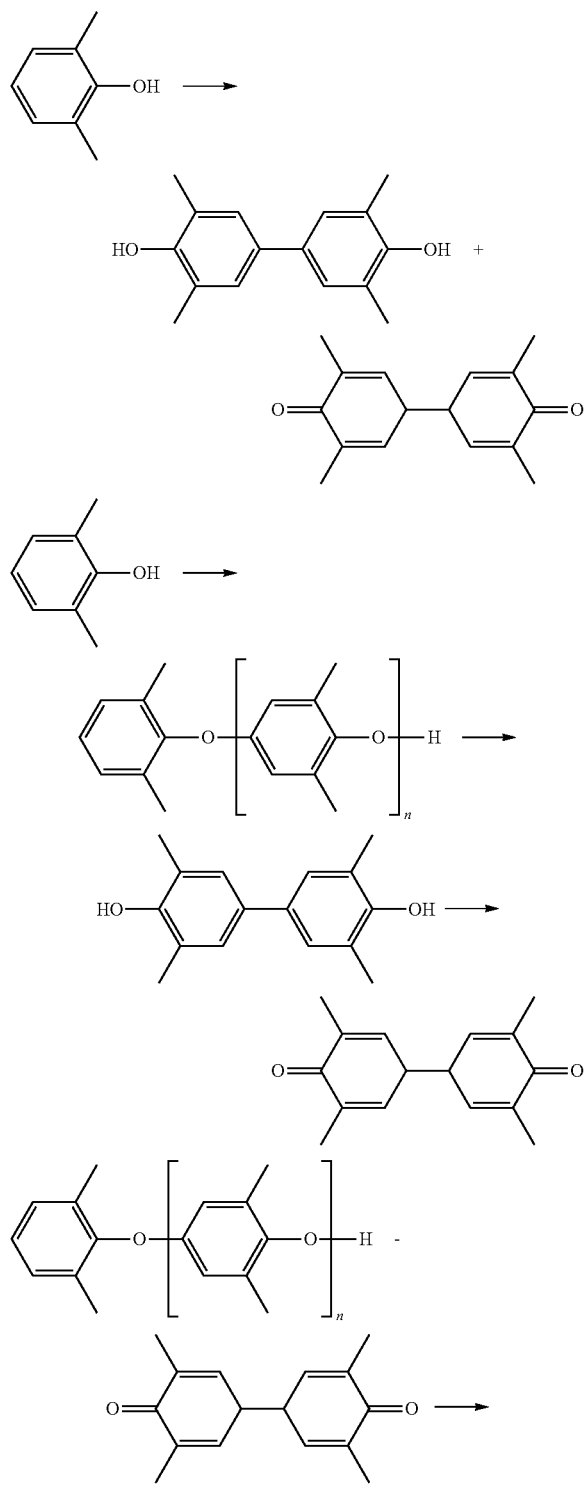

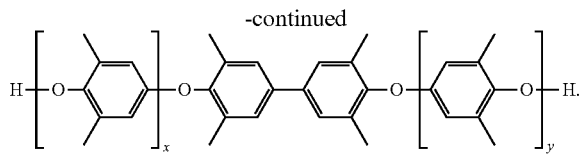

15 Claims, 1 Drawing Sheet

(51) Int. Cl.
*C07C 37/11* (2006.01)
*C08G 65/48* (2006.01)
*C08G 65/44* (2006.01)

(56) References Cited

U.S. PATENT DOCUMENTS

| | | |
|---|---|---|
| 3,914,266 A | 10/1975 | Hay |
| 4,028,341 A | 6/1977 | Hay |
| 4,092,294 A | 5/1978 | Bennett, Jr. et al. |
| 4,140,675 A | 2/1979 | White |
| 4,165,422 A | 8/1979 | White |
| 4,234,706 A | 11/1980 | White |
| 4,477,649 A | 10/1984 | Mobley |
| 6,307,010 B1 | 10/2001 | Braat et al. |
| 6,689,920 B2 | 2/2004 | Ishii et al. |
| 6,835,785 B2 | 12/2004 | Ishii et al. |
| 7,329,708 B2 | 2/2008 | Birsak et al. |
| 7,655,278 B2 | 2/2010 | Braidwood et al. |
| 7,786,219 B2 | 8/2010 | Ishii et al. |
| 8,053,077 B2 | 11/2011 | Braidwood et al. |
| 8,288,501 B2 | 10/2012 | Maeda et al. |
| 8,357,769 B2 | 1/2013 | Maeda et al. |
| 2006/0160982 A1 | 7/2006 | Ishii |
| 2009/0062478 A1 | 3/2009 | Carrillo |
| 2012/0149865 A1* | 6/2012 | Maeda .................. C08G 65/44 528/215 |

OTHER PUBLICATIONS

Vakhitova, M. Sh. et al., "Oxidation of 2,6-disubstituted phenols as a route to 3,5,3,5-tetrasubstituted diphenoquinones and 4,4-dihydroxydiphenyls," Bulletin of the Academy of Sciences of the USSR, Division of Chemical Sciences; Aug. 1, 1987, vol. 36, No. 8,pp. 1675-1677.

Nava, Hildeberto et al.,"Functional Polymers and Sequential Copolymers by Phase Transfer Catalysis", Journal of Polymer Science: Part A: Polymer Chemistry; 1986, pp. 965-990, vol. 24.

Percec, Virgil et al, "Synthesis of a,w-bis(2,6-dimethylphenol)-poly(2,6-dimethyl-1,4-phenylene oxide) by phase transfer catalyzed polymerization of 4-bromo-2,6-dimethylphenol in the presence of 2,2-di(4-hydroxy-3,5-dimethylphenyl)propane," Polymer Bulletin; 1990, pp. 493-500, 24.

White, "Reactions of Poly(phenylene Oxide)s with Quinones. I. The Quinone-Coupling Reaction Between Low Molecular Weight Poly(2,6-Dimethyl-1,4-Phenylene Oxide) and 3,3',5,5'-Tetramethyl-4,4'-Diphenoquinone", Journal of Polymer Science: Polymer Chemistry Edition; 1981, pp. 1367-1383, vol. 19.

Written Opinion; International Application No. PCT US2016 061254; Int'l Filing Date: Nov. 10, 2016; 6 pages.

* cited by examiner

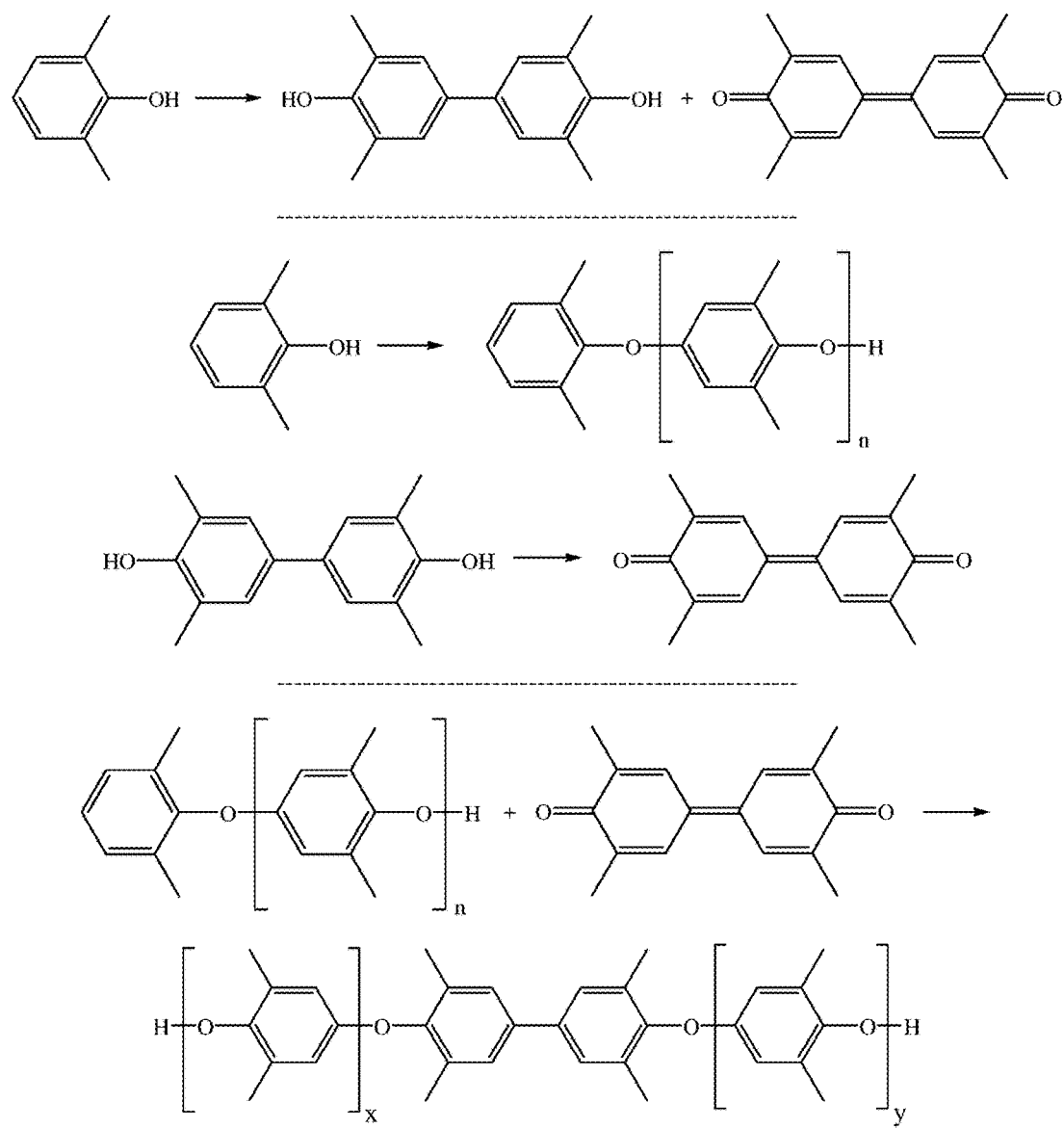

METHOD OF FORMING PHENYLENE ETHER OLIGOMER

CROSS-REFERENCE TO RELATED APPLICATIONS

This application is a National Stage application of PCT/US2016/061254, filed Nov. 10, 2016, which claims the benefit of U.S. Provisional Application No. 62/266,749, filed Dec. 14, 2015, both of which are incorporated by reference herein in their entirety.

BACKGROUND OF THE INVENTION

Phenylene ether oligomers have demonstrated utility in thermoset compositions for electronics fabrication. The thermoset compositions benefit from the oligomers' high glass transition temperature, high toughness, low dielectric properties, and low water absorption. Particular advantages have been observed for bifunctional oligomers comprising, on average, about two hydroxyl groups per molecule. Such bifunctional oligomers can be prepared by copolymerizing a monohydric phenol, such as 2,6-dimethylphenol, with a dihydric phenol, such as 2,2-bis(4-hydroxy-3,5-dimethyl)propane. See, e.g., U.S. Pat. No. 7,655,278 B2 to Braidwood et al. However, use of the dihydric phenol adds substantially to cost, and there is a desire for bifunctional phenylene ether oligomers that can be readily prepared at lower cost and lower molecular weight.

Bifunctional poly(phenylene ether)s have also been prepared by reaction of a poly(phenylene ether), such as poly(2,6-dimethyl-1,4-phenylene ether), with a diphenoquinone, such as 3,3',5,5'-tetramethyldiphenoquinone. See, e.g., U.S. Pat. No. 4,140,675 to White. However, in practice such methods have not been amenable to producing low molecular weight oligomers.

There remains a need for a process of forming bifunctional phenylene ether oligomers using diphenoquinone generated primarily or entirely in situ, rather than using a dihydric phenol.

BRIEF SUMMARY OF EMBODIMENTS OF THE INVENTION

One embodiment is a method of forming a phenylene ether oligomer, the method comprising: reacting 2,6-dimethylphenol in the presence of toluene, oxygen, copper ion, bromide ion, and an alkylenediamine to form a first reaction mixture comprising 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof; wherein weight percent values are based on the weight of initial 2,6-dimethylphenol; and wherein the reaction of the 2,6-dimethylphenol is conducted at a mole ratio of 2,6-dimethylphenol to copper ion of 300:1 to 1000:1, at a mole ratio of alkylenediamine to copper ion of 2:1 to 8:1, in the presence of 0 to 0.2 weight percent of tertiary monoamine, based on the weight of toluene, and at a temperature of 50 to 110° C.; reacting the residual 2,6-dimethylphenol in the presence of toluene, oxygen, copper ion, bromide ion, and alkylenediamine to form a second reaction mixture comprising 40 to 90 weight percent poly(2,6-dimethyl-1,4-phenylene ether); wherein the reacting residual 2,6-dimethylphenol is conducted at a temperature of 25 to 60° C.; and wherein any 3,3',5,5'-tetramethyl-4,4'-dihydroxybiphenyl present in the first reaction mixture is substantially converted to 3,3',5,5'-tetramethyldiphenoquinone in the second reaction mixture; chelating the copper ion; and reacting the poly(2,6-dimethyl-1,4-phenylene ether) and the 3,3',5,5'-tetramethyldiphenoquinone to form a phenylene ether oligomer having the structure

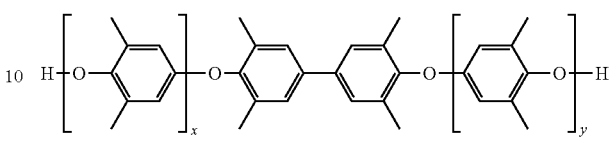

wherein x and y are independently 0 to 20, provided that the sum of x and y is at least 1 and no greater than 30; wherein the reacting the poly(2,6-dimethyl-1,4-phenylene ether) and the 3,3',5,5'-tetramethyldiphenoquinone is conducted at a temperature of 50 to 100° C.

This and other embodiments are described in detail below.

BRIEF DESCRIPTION OF THE DRAWING

The FIGURE is a chemical scheme for a three-step process for forming a bifunctional poly(phenylene ether) using diphenoquinone generated in situ.

DETAILED DESCRIPTION OF THE INVENTION

Bifunctional poly(phenylene ether) (PPE) oligomers have been synthesized using a process that first partially converts 2,6-dimethylphenol to 3,3',5,5'-tetramethyl-4,4'-dihydroxybiphenyl and/or 3,3',5,5'-tetramethyldiphenoquinone, then converts residual 2,6-dimethylphenol to poly(phenylene ether) and simultaneously oxidizes any 3,3',5,5'-tetramethyl-4,4'-dihydroxybiphenyl to 3,3',5,5'-tetramethyldiphenoquinone, and then reacts the poly(phenylene ether) with the 3,3',5,5'-tetramethyldiphenoquinone to form bifunctional phenylene ether oligomer. The reaction steps can be carried out sequentially in the same reaction vessel, without isolation of intermediates.

The FIGURE is a chemical scheme for the three-step process. For brevity, the term "Step 1" is used to refer to the partial conversion of 2,6-dimethylphenol to 3,3',5,5'-tetramethyl-4,4'-dihydroxybiphenyl and/or 3,3',5,5'-tetramethyldiphenoquinone. Step 1 corresponds to the top section of the FIGURE. "Step 2" refers to the conversion of residual 2,6-dimethylphenol to poly(phenylene ether) and simultaneous oxidation of any 3,3',5,5'-tetramethyl-4,4'-dihydroxybiphenyl to 3,3',5,5'-tetramethyldiphenoquinone. Step 2 corresponds to the middle section of the FIGURE. "Step 3" refers to the reaction of the poly(phenylene ether) with the 3,3',5,5'-tetramethyldiphenoquinone to form bifunctional phenylene ether oligomer. Step 3 corresponds to the lower section of the FIGURE. Use of the terms "Step 1", "Step 2", and "Step 3" does not mean that prior steps, intermediate steps, or later steps are excluded. For example, the method includes chelation of copper ion is conducted between Step 2 and Step 3, and the method can include isolation of the phenylene ether oligomer after Step 3.

One embodiment is a method of forming a phenylene ether oligomer, the method comprising: reacting 2,6-dimethylphenol (i.e., "initial 2,6-dimethylphenol") in the presence of toluene, oxygen, copper ion, bromide ion, and an alkylenediamine to form a first reaction mixture comprising 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof; wherein weight percent values are based on the weight of initial 2,6-dimethylphenol; and wherein the reaction of the 2,6-dimethylphenol is conducted at a mole ratio of 2,6-dimethylphenol to copper ion of 300:1 to 1000:1; at a mole ratio of alkylenediamine to copper ion of 2:1 to 8:1 in the presence of 0 to 0.2 weight percent of tertiary monoamine, based on the weight of toluene; and at a temperature of 50 to 110° C.; reacting the residual 2,6-dimethylphenol in the presence of toluene, oxygen, copper ion, bromide ion, and alkylenediamine to form a second reaction mixture comprising 40 to 90 weight percent poly(2,6-dimethyl-1,4-phenylene ether); wherein the reacting residual 2,6-dimethylphenol is conducted at a temperature of 25 to 60° C.; and wherein any 3,3',5,5'-tetramethyl-4,4'-dihydroxybiphenyl present in the first reaction mixture is substantially converted to 3,3',5,5'-tetramethyldiphenoquinone in the second reaction mixture; chelating the copper ion; and reacting the poly(2,6-dimethyl-1,4-phenylene ether) and the 3,3',5,5'-tetramethyldiphenoquinone to form a phenylene ether oligomer having the structure

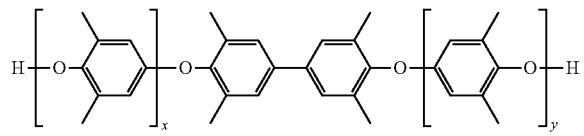

wherein x and y are independently 0 to 20, provided that the sum of x and y is at least 1 and no greater than 30; wherein the reacting the poly(2,6-dimethyl-1,4-phenylene ether) and the 3,3',5,5'-tetramethyldiphenoquinone is conducted at a temperature of 50 to 100° C.

In Step 1, 2,6-dimethylphenol (i.e., "initial 2,6-dimethylphenol") is reacted in the presence of toluene, oxygen, copper ion, bromide ion, and an alkylenediamine to form a first reaction mixture comprising, based on the weight of initial 2,6-dimethylphenol, 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof.

2,6-Dimethylphenol, also known as 2,6-xylenol, is the monomer.

Toluene is a solvent and can, optionally, be the only solvent. In this context it will be understood that amine reagents and reaction product water are not considered solvents.

Oxygen, which refers to molecular oxygen ($O_2$), is an oxidant required for the oxidative dimerization and polymerization of Steps 1 and 2.

Copper ion, which refers to total copper ion, including uncomplexed $Cu^+$, complexed $Cu^+$, uncomplexed $Cu^{2+}$, complexed $Cu^{2+}$, and combinations thereof, catalyzes oxidative dimerization and polymerization of 2,6-dimethylphenol. It will be understood that the oxidative nature of the Step 1 and Step 2 reactions requires that the copper catalyst shuttles between the +1 and +2 oxidation states, and that the copper ion can be in either of these oxidation states when initially provided. Suitable sources of copper ion include cuprous chloride, cupric chloride, cuprous bromide, cupric bromide, cuprous sulfate, cupric sulfate, cuprous acetate, and cupric acetate.

Bromide ion complexes with copper ion. Sources of bromide ion include hydrobromic acid, cuprous bromide, cupric bromide, alkali metal bromides (including sodium bromide and potassium bromide), alkaline earth metal bromides, and combinations thereof. The present inventors have also found that the bromide ion source hydrobromic acid is useful for reacting with tertiary amine impurities in recycled toluene to form tertiary ammonium bromide. The tertiary amine impurities would otherwise interfere with formation of the C—C coupled products 3,3',5,5'-tetramethyl-4,4'-dihydroxybiphenyl and 3,3',5,5'-tetramethyldiphenoquinone. In some embodiments, bromide ion is used at a concentration sufficient to provide a mole ratio of bromide ion to copper ion of 1:1 to 20:1, specifically 2:1 to 10:1. It will be understood that in these mole ratios, "bromide ion" refers to total bromide ion (including free and complexed forms), and "copper ion" refers to total copper ion (including free and complexed forms). This paragraph's statements about bromide ion source and amount refer to both Step 1 and Step 2.

Alkylenediamine forms a complex with copper ion that is an active catalyst for oxidative dimerization and polymerization of 2,6-dimethylphenol. In general, the alkylenediamine, has two or three carbon atoms separating the two nitrogen atoms, and each of its two nitrogen atoms can be substituted with zero, one, or two alkyl groups. As used herein, the term "alkyl" includes linear alkyl, branched alkyl, cyclic alkyl, and combinations of linear and branched alkyl, linear and cyclic alkyl, branched and cyclic alkyl, and linear and branched and cyclic alkyl. Classes of suitable alkylenediamines include N,N'-di-($C_{1-12}$-alkyl)ethylenediamines, N,N,N'-tri-($C_{1-12}$-alkyl)ethylenediamines, N,N,N'N'-tetra-($C_{1-12}$-alkyl)ethylenediamines, N,N'-di-($C_{1-12}$-alkyl)-1,2-propylenediamines, N,N,N'-tri-($C_{1-12}$-alkyl)-1,2-propylenediamines, N,N,N'N'-tetra-($C_{1-12}$-alkyl)-1,2-propylenediamines, N,N'-di-($C_{1-12}$-alkyl)-1,3-propylenediamines, N,N,N'-tri($C_{1-12}$-alkyl)-1,3-propylenediamines, N,N,N'N'-tetra-($C_{1-12}$-alkyl)-1,3-propylenediamines, and combinations thereof. Specific alkylenediamines include N,N'-di-tert-butylethylenediamine, N,N,N',N'-tetraethylethylenediamine, N,N,N',N'-tetramethylethylenediamine, N,N'-diethyl-N,N'-dimethylethylenediamine, N,N'-diethylethylenediamine, N,N'-dimethylethylenediamine, N,N,N',N'-tetramethyl-1,3-butylenediamine, and combinations thereof.

The Step 1 reaction of 2,6-dimethylphenol is conducted at a mole ratio of 2,6-dimethylphenol to copper ion of 300:1 to 1000:1. Within this range, the mole ratio of 2,6-dimethylphenol to copper ion can be 400:1 to 900:1, specifically 400:1 to 800:1, more specifically 500:1 to 700:1. The term "copper ion" refers to total copper ion, including $Cu^+$ and $Cu^{2+}$, complexed or uncomplexed.

The Step 1 reaction is also conducted at a mole ratio of alkylenediamine to copper ion of 2:1 to 8:1. Within this range, the mole ratio of alkylenediamine to copper ion can be 3:1 to 5:1, specifically 3.5:1 to 4.5:1. The present inventors have unexpectedly observed that mole ratios of alkylenediamine to copper ion less than 3:1 are associated with reduced yields of the tail-to-tail dimer species 3,3',5,5'-tetramethyl-4,4'-dihydroxybiphenyl and 3,3',5,5'-tetramethyldiphenoquinone.

Tertiary monoamines, such as dimethyl-n-butylamine, are common constituents of copper-based catalysts for poly(phenylene ether) synthesis. See, for example, U.S. Pat. Nos. 3,306,874 and 3,306,875 to Hay, and 4,092,294 to Bennett et al. However, the present inventors have unexpectedly observed that tertiary monoamines interfere with the Step 1 formation of 3,3',5,5'-tetramethyl-4,4'-dihydroxybiphenyl and 3,3',5,5'-tetramethyldiphenoquinone. The present method therefore requires that tertiary monoamines are either absent, or present at no more than 0.2 weight percent, based on the weight of toluene. The upper limit for tertiary monoamine concentration in Step 1 can be 0.1 weight percent, specifically 0.05 weight percent. Alternatively, the tertiary monoamine content can be expressed as a mole ratio to copper. For example, the Step 1 reaction mixture can contain 0 to 5 moles tertiary monoamine per mole copper. Within this range, the mole ratio of tertiary monoamine to copper can be 1:1, specifically 0.1 to 1, more specifically 0 to 1. As noted above, the present inventors have determined that adverse effects of tertiary monoamine in the Step 1 reaction mixture can be ameliorated by hydrobromic acid, which converts the tertiary monoamines to their corresponding tertiary ammonium bromides.

Secondary monoamines, such as di-n-butylamine, are also common constituents of copper-based catalysts for poly (phenylene ether) synthesis. See, for example, U.S. Pat. Nos. 3,306,874 and 3,306,875 to Hay, and 4,092,294 to Bennett et al. Although less potent than tertiary monoamines, secondary monoamines have been unexpectedly observed to interfere with the Step 1 formation of 3,3',5,5'-tetramethyl-4,4'-dihydroxybiphenyl and 3,3',5,5'-tetramethyldiphenoquinone. It is therefore desirable to minimize or eliminate their presence in the Step 1 reaction mixtures. Thus, in some embodiments, the Step 1 reaction is conducted in the presence of 0 to 1 weight percent secondary monoamine, based on the weight of 2,6-dimethylphenol. Within this range, the upper limit can be 0.05 weight percent, and a value of zero weight percent is preferred.

The Step 1 reaction is conducted at a temperature of 50 to 110° C. Within this range, the temperature can be 55 to 100° C., specifically 70 to 90° C., more specifically 80 to 90° C. The Step 1 reaction time will vary according to the desired product molecular weight characteristics but is generally 30 to 160 minutes.

In some embodiments, the Step 1 reaction is conducted at 20 to 40 percent solids. Percent solids is the weight percent 2,6-dimethylphenol based on the total of toluene and 2,6-dimethylphenol. It is preferred to use 25 to 35 percent solids in the Step 1 reaction.

The product of Step 1 is a first reaction mixture comprising, based on the weight of initial 2,6-dimethylphenol, 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof. Within these ranges, the amount of residual 2,6-dimethylphenol can be 40 to 80 weight percent, specifically 50 to 80 weight percent, and the amount of 3,3',5,5'-tetramethyl-4,4'-dihydroxybiphenyl, 3,3',5,5'-tetramethyldiphenoquinone, or a combination thereof can be 20 to 60 weight percent, specifically 20 to 50 weight percent.

In Step 2, the residual 2,6-dimethylphenol from Step 1 is reacted in the presence of toluene, oxygen, copper ion, bromide ion, and alkylenediamine to form a second reaction mixture comprising 40 to 90 weight percent poly(2,6-dimethyl-1,4-phenylene ether). The Step 2 reaction is conducted at a temperature of 25 to 60° C. Within this range, the reaction temperature can be 30 to 45° C., specifically 35 to 45° C. The reaction time for Step 2 will vary according to the desired molecular weight characteristics of the product but is generally 30 to 160 minutes, specifically 40 to 100 minutes. In Step 2, not only is the residual 2,6-dimethylphenol polymerized to poly(2,6-dimethyl-1,4-phenylene ether), any 3,3',5,5'-tetramethyl-4,4'-dihydroxybiphenyl present in the first reaction mixture is substantially converted (oxidized) to 3,3',5,5'-tetramethyldiphenoquinone in the second reaction mixture. It is possible modify the catalyst composition in Step 2 relative to Step 1, but it is both possible and economical to use the same catalyst composition for both steps.

Between Step 2 and Step 3, the copper ion is chelated. This means that copper ion is associated with a chelating agent that has greater affinity for copper ion than any of the amine ligands used in Step 1 and Step 2. Copper chelation is a well-known step in poly(phenylene ether) synthesis, and suitable chelating agents are known. These include ethylenediaminetetraacetic acid and its alkali metal salts, and nitrilotriacetic acid and its alkali metal salts. A currently preferred chelating agent is trisodium nitrilotriacetate. Once chelated, the copper ion can be separated from the reaction mixture (e.g., by removing the aqueous phase), or it can remain in the reaction mixture. Specifically, reacting the poly(2,6-dimethyl-1,4-phenylene ether) and the 3,3',5,5'-tetramethyldiphenoquinone is conducted in the presence of the chelated copper ion.

In Step 3, the poly(2,6-dimethyl-1,4-phenylene ether) and the 3,3',5,5'-tetramethyldiphenoquinone from the second reaction mixture are reacted to form a phenylene ether oligomer. This is a known reaction, described, for example, in Dwain M. White, "Reactions of Poly(phenylene Oxide)s with Quinones. I. The Quinone-Coupling Reaction Between Low-Molecular-Weight Poly(2,6-Dimethyl-1,4-Phenylene Oxide) and 3,3',5,5'-Tetramethyl-4,4'-Diphenoquinone", *Journal of Polymer Science: Polymer Chemistry Edition*, 1981, volume 19, 1367-1383. The phenylene ether oligomer has the structure

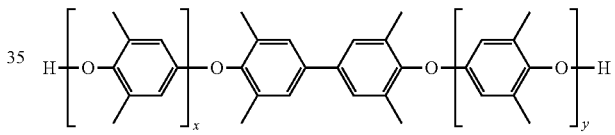

wherein x and y are independently 0 to 20, provided that the sum of x and y is at least 1 and no greater than 30. In some embodiments, the sum of x and y is no greater than 25, specifically no greater than 20. The Step 3 reaction is conducted at a temperature of 50 to 100° C. Within this range, the temperature can be 70 to 90° C., specifically 80 to 90° C. Under these conditions, the reaction is typically completed in 2 to 8 hours. The Step 3 reaction is preferably conducted in an inert atmosphere, such as nitrogen or argon.

It is an advantage of the present method that each step can be conducted in toluene solvent. Mixed solvents, such as the mixtures of aromatic solvents and aliphatic alcohols used in some poly(phenylene ether) synthesis methods, are not required. In some embodiments, the reacting the 2,6-dimethylphenol and the reacting the residual 2,6-dimethylphenol are conducted in the absence of any solvent other than toluene. In this context it will be understood that amine reagents and reaction product water are not considered solvents.

In a very specific embodiment of the method, the alkylenediamine comprises N,N'-di-tert-butylethylenediamine; the reacting 2,6-dimethylphenol is conducted at a mole ratio of 2,6-dimethylphenol to copper ion of 400:1 to 800:1, at a mole ratio of N,N'-di-tert-butylethylenediamine to copper ion of 3:1 to 5:1, in the presence of 0 to 0.1 weight percent secondary monoamine, based on the weight of 2,6-dimethylphenol, and at a temperature of 70 to 90° C.; the first reaction mixture comprises 40 to 80 weight percent residual 2,6-dimethylphenol, and 20 to 60 weight percent 3,3',5,5'-tetramethyl-4,4'-dihydroxybiphenyl, 3,3',5,5'-tetramethyldiphenoquinone, or a combination thereof, based on the weight of initial 2,6-dimethylphenol; the reacting residual 2,6-dimethylphenol is conducted at a temperature of 30 to 45° C.; the reacting the poly(2,6-dimethyl-1,4-phenylene ether) and the 3,3',5,5'-tetramethyldiphenoquinone is conducted at a temperature of 70 to 90° C.; and the sum of x and y is less than or equal to 20.

The invention includes at least the following embodiments.

Embodiment 1:

A method of forming a phenylene ether oligomer, the method comprising: reacting 2,6-dimethylphenol in the presence of toluene, oxygen, copper ion, bromide ion, and an alkylenediamine to form a first reaction mixture comprising 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof; wherein weight percent values are based on the weight of initial 2,6-dimethylphenol; and wherein the reaction of the 2,6-dimethylphenol is conducted at a mole ratio of 2,6-dimethylphenol to copper ion of 300:1 to 1000:1, at a mole ratio of alkylenediamine to copper ion of 2:1 to 8:1, in the presence of 0 to 0.2 weight percent of tertiary monoamine, based on the weight of toluene, and at a temperature of 50 to 110° C.; reacting the residual 2,6-dimethylphenol in the presence of toluene, oxygen, copper ion, bromide ion, and alkylenediamine to form a second reaction mixture comprising 40 to 90 weight percent poly(2,6-dimethyl-1,4-phenylene ether); wherein the reacting residual 2,6-dimethylphenol is conducted at a temperature of 25 to 60° C.; and wherein any 3,3',5,5'-tetramethyl-4,4'-dihydroxybiphenyl present in the first reaction mixture is substantially converted to 3,3',5,5'-tetramethyldiphenoquinone in the second reaction mixture; chelating the copper ion; and reacting the poly(2,6-dimethyl-1,4-phenylene ether) and the 3,3',5,5'-tetramethyldiphenoquinone to form a phenylene ether oligomer having the structure

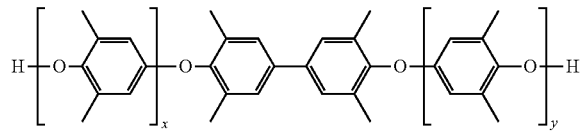

wherein x and y are independently 0 to 20, provided that the sum of x and y is at least 1 and no greater than 30; wherein the reacting the poly(2,6-dimethyl-1,4-phenylene ether) and the 3,3',5,5'-tetramethyldiphenoquinone is conducted at a temperature of 50 to 100° C.

Embodiment 2: The method of embodiment 1, wherein the alkylenediamine is selected from the group consisting of N,N'-di-($C_{1-12}$-alkyl)ethylenediamines, N,N,N'-tri-($C_{1-12}$-alkyl)ethylenediamines, N,N,N'N'-tetra-($C_{1-12}$-alkyl)ethylenediamines, N,N'-di-($C_{1-12}$-alkyl)-1,2-propylenediamines, N,N,N'-tri-($C_{1-12}$-alkyl)-1,2-propylenediamines, N,N,N'N'-tetra-($C_{1-12}$-alkyl)-1,2-propylenediamines, N,N'-di-($C_{1-12}$-alkyl)-1,3-propylenediamines, N,N,N'-tri-($C_{1-12}$-alkyl)-1,3-propylenediamines, N,N,N'N'-tetra-($C_{1-12}$-alkyl)-1,3-propylenediamines, and combinations thereof.

Embodiment 3: The method of embodiment 1 or 2, wherein the alkylenediamine is selected from the group consisting of N,N'-di-tert-butylethylenediamine, N,N,N',N'-tetraethylethylenediamine, N,N,N',N'-tetramethylethylenediamine, N,N'-diethyl-N,N'-dimethylethylenediamine, N,N'-diethylethylenediamine, N,N'-dimethylethylenediamine, N,N,N',N'-tetramethyl-1,3-butylenediamine, and combinations thereof.

Embodiment 4: The method of any one of embodiments 1-3, wherein the reaction of the 2,6-dimethylphenol is conducted at a mole ratio of 2,6-dimethylphenol to copper ion of 400:1 to 900:1.

Embodiment 5: The method of any one of embodiments 1-4, wherein the reaction of the 2,6-dimethylphenol is conducted in the presence of 0 to 0.1 weight percent tertiary monoamine, based on the weight of toluene.

Embodiment 6: The method of any one of embodiments 1-5, wherein the reaction of the 2,6-dimethylphenol is conducted at a mole ratio of alkylenediamine to copper ion of 3:1 to 6:1.

Embodiment 7: The method of any one of embodiments 1-6, wherein the reaction of the 2,6-dimethylphenol is conducted at a temperature of 55 to 100° C.

Embodiment 8: The method of any one of embodiments 1-7, wherein the reaction of the 2,6-dimethylphenol is conducted in the presence of 0 to 1 weight percent secondary monoamine, based on the weight of 2,6-dimethylphenol.

Embodiment 9: The method of any one of embodiments 1-8, wherein the first reaction mixture comprises 40 to 80 weight percent residual 2,6-dimethylphenol, and 20 to 60 weight percent 3,3',5,5'-tetramethyl-4,4'-dihydroxybiphenyl, 3,3',5,5'-tetramethyldiphenoquinone, or a combination thereof, wherein weight percent values are based on the weight of initial 2,6-dimethylphenol.

Embodiment 10: The method of any one of embodiments 1-9, wherein the reacting residual 2,6-dimethylphenol is conducted at a temperature of 30 to 45° C.

Embodiment 11: The method of any one of embodiments 1-10, wherein the reacting the poly(2,6-dimethyl-1,4-phenylene ether) and the 3,3',5,5'-tetramethyldiphenoquinone is conducted at a temperature of 70 to 90° C.

Embodiment 12: The method of any one of embodiments 1-11, wherein the reacting the 2,6-dimethylphenol and the reacting the residual 2,6-dimethylphenol are conducted in the absence of any solvent other than toluene.

Embodiment 13: The method of any one of embodiments 1-12, wherein the reacting the poly(2,6-dimethyl-1,4-phenylene ether) and the 3,3',5,5'-tetramethyldiphenoquinone is conducted in the presence of the chelated copper ion.

Embodiment 14: The method of any one of embodiments 1-13, wherein the sum of x and y is less than or equal to 20.

Embodiment 15: The method of embodiment 1, wherein the alkylenediamine comprises N,N'-di-tert-butylethylenediamine; wherein the reaction of the 2,6-dimethylphenol is conducted at a mole ratio of 2,6-dimethylphenol to copper ion of 400:1 to 800:1, at a mole ratio of N,N'-di-tert-butylethylenediamine to copper ion of 3:1 to 5:1, in the presence of 0 to 0.1 weight percent secondary monoamine, based on the weight of 2,6-dimethylphenol, and at a temperature of 70 to 90° C.; wherein the first reaction mixture comprises 40 to 80 weight percent residual 2,6-dimethylphenol, and 20 to 60 weight percent 3,3',5,5'-tetramethyl-4,4'-dihydroxybiphenyl, 3,3',5,5'-tetramethyldiphenoquinone, or a combination thereof, based on the weight of initial 2,6-dimethylphenol; wherein the reacting residual 2,6-dimethylphenol is conducted at a temperature of 30 to 45° C.; wherein the reacting the poly(2,6-dimethyl-1,4-phenylene ether) and the 3,3',5,5'-tetramethyldiphenoquinone is conducted at a temperature of 70 to 90° C.; and wherein the sum of x and y is less than or equal to 20.

All ranges disclosed herein are inclusive of the endpoints, and the endpoints are independently combinable with each other. Each range disclosed herein constitutes a disclosure of any point or sub-range lying within the disclosed range.

The invention is further illustrated by the following non-limiting examples.

WORKING EXAMPLES

Reagents used in the working examples are summarized in Table 1.

TABLE 1

| Component | Description |
|---|---|
| DMP | 2,6-Dimethylphenol, CAS Reg. No. 576-26-1; obtained from Sigma Aldrich. |
| CuBr | Cuprous bromide, CAS reg. No. 7787-70-4; obtained from S D Fine-Chem Limited. |
| $Cu_2O$ | Cuprous oxide, CAS Reg. No. 1317-39-1; obtained from Sigma Aldrich. |
| HBr | Hydrobromic acid, CAS Reg. No. 10035-10-6; obtained from S D Fine-Chem Limited. |
| DBEDA | N,N'-Di-tert-butylethylenediamine, CAS Reg. No. 4062-60-6; obtained from Fluka. |
| TEEDA | N,N,N',N'-Tetraethylethylenediamine, CAS Reg. No. 110-18-9; obtained from Sigma Aldrich. |
| DBA | Di-n-butylamine, CAS Reg. No. 111-92-2; obtained from Sigma Aldrich |
| DMBA | N,N-Dimethylbutylamine, CAS Reg. No. 927-62-8; obtained from Sigma Aldrich |
| DDDMAC | N,N,N',N'-Didecyldimethylammonium chloride, CAS Reg. No. 7173-51-5; obtained from Sigma Aldrich. |
| NTA | Nitrilotriacetic acid trisodium salt, CAS Reg. No. 5064-31-3; obtained from Sigma Aldrich. |
| MEK | Methyl ethyl ketone, CAS Reg. No. 78-93-3, obtained from Merck. |
| Toluene | Toluene, CAS Reg. No. 108-33-3; obtained from Sigma Aldrich. |

Example 1

This example illustrates the synthesis of a phenylene ether oligomer having an intrinsic viscosity of about 0.09 deciliter per gram, and a hydroxyl content of greater than 1.9 hydroxyl groups per molecule. The synthesis employed N,N,N',N'-tetraethylethylenediamine as the alkylenediamine. The reaction was conducted in a jacketed 0.25 liter reactor equipped with an overhead stirrer, nitrogen inlet, oxygen inlet, and water jacket for cooling and heating. The same reactor was used for all examples.

Step 1
A. The reactor was set to 85° C. and the purge nitrogen flow was kept at 800 standard cubic centimeter per minute (sccm).
B. 20 grams of 2,6-dimethylphenol (DMP) was dissolved in 30 grams toluene at room temperature, on a magnetic stirrer in fifteen minutes and was added to the reactor.
C. The amines TEEDA (0.04 gram), DBA (0.29 gram) and DDDMAC (0.025 gram) in 10 grams toluene solution were added first to 0.04 gram CuBr and thoroughly shaken until a homogenous green solution was obtained. All weighing vessels were rinsed with 10 grams of toluene, which were added to the reactor.
D. Once the reactor was filled and closed and at a reaction mass temperature of 85° C., the oxygen flow was started at 300 sccm.

Step 2
A. At 60 minutes, the cooling bath temperature was reduced to 30° C. The dimers 3,3',5,5'-tetramethyl-4,4'-dihydroxybiphenyl (also known as 3,3',5,5'-tetramethyl-4,4'-biphenol, or TMBP) and 3,3',5,5'-tetramethyldiphenoquinone (TMDQ) precipitate under these conditions.
B. TEEDA (0.08 gram), DBA (0.39 gram) and DMBA (2.74 gram) in 10 grams toluene solution were added first to 0.054 g CuBr and thoroughly shaken until a homogenous green solution was obtained. All weighing vessels were rinsed with 10 g of toluene, which were added to the reactor.
C. The oxygen flow was stepwise lowered to 200 sccm until the end of the reaction, which was 120 minutes later. The oxygen flow was stopped at this point.

Step 3
A. After the 120 minutes of Step 2, the recirculating water bath temperature was again raised to 85° C., at which point 0.45 grams of NTA and 5 grams of water per 100 grams of reaction mixture were added. The mixture was stirred for 240 minutes under a nitrogen purge of 50 sccm (to incorporate the TMDQ into the PPE) and afterward allowed to sit overnight at 60° C. to allow phase separation.
B. The water phase was removed and the toluene phase was centrifuged for 30 minutes at 3000 rotations per minute (rpm) in a 23° C. thermostatted centrifuge. The light phase was then totally isolated by evaporation overnight in a vacuum oven at 100° C.

The isolated phenylene ether oligomer had an intrinsic viscosity of 0.085 deciliter per gram, measured by Ubbelohde viscometer in chloroform at 25° C.

Example 2

This example illustrates the synthesis of a PPE oligomer having an intrinsic viscosity of about 0.05 deciliter per gram, and a hydroxyl content of greater than 1.9 hydroxyl groups per molecule. This example includes many experimental variations that collectively illustrate the factors that affect the yield of C—C coupling in the first step.

A reaction scheme for the three-step, one-pot process is provided as FIG. 1.

For synthesizing an oligomer with an intrinsic viscosity of about 0.05 deciliter/gram, relatively higher amounts of C—C products were produced in Step 1 by increasing the reaction time to 70 minutes at a monomer:copper mole ratio of 400. This was followed by polymerization time of 60 minutes with no further addition of copper in order to limit the chain growth in Step 2.

One factor affecting the yield of C—C coupling is the concentration of the ligand DBEDA. Reaction conditions with varying DBEDA concentrations are summarized in Table 2, where all component amounts are expressed in units of grams. Held constant were a reaction temperature of 85° C., an $O_2$ flow rate of 300 sccm, and a percent solids of 30 weight percent.

The results, presented in Table 3, show that decreases in the mole ratio of DBEDA to copper are associated with decreases in the yield of C—C coupling, as well as increases in the mole ratio of reduced to oxidized C—C coupling products.

TABLE 2

|  | Ex. 2a | Ex. 2b | Ex. 2c |
| --- | --- | --- | --- |
| 2,6 DMP | 30.0000 | 30.0000 | 30.0000 |
| DBEDA | 0.2820 | 0.4230 | 0.5650 |
| Toluene | 68.0000 | 68.0000 | 68.0000 |
| $Cu_2O$ | 0.0585 | 0.0585 | 0.0585 |
| HBr | 0.7374 | 0.7374 | 0.7374 |
| DDDMAC | 0.0500 | 0.0500 | 0.0500 |
| subtotal | 99.1309 | 99.2689 | 99.4109 |
| NTA | 0.4204 | 0.4204 | 0.4204 |
| $H_2O$ | 5.0020 | 5.0020 | 5.0020 |

TABLE 3

|  | mole ratio Cu:HBr | mole ratio DBEDA:Cu | mole ratio DMP:Cu | C-C yield (%) | TMBP/TMDQ |
| --- | --- | --- | --- | --- | --- |
| Ex. 2a | 1:1 | 4.0099 | 300.2961 | 46.0000 | 1.2322 |
| Ex. 2b | 1:1 | 3.0021 | 300.2961 | 33.3333 | 1.3142 |
| Ex. 2c | 1:1 | 2.0014 | 300.2961 | 26.6667 | 2.4187 |

The mole ratio of DMP monomer to copper is another factor affecting the yield of C—C coupling. Reaction conditions varying this ratio are summarized in Table 4, where all component amounts are expressed in units of grams. Held constant were a reaction temperature of 85° C., an $O_2$ flow rate of 300 sccm, and a percent solids of 30 weight percent.

The results in Table 5 show that higher copper concentrations are associated with more C—C coupling. The yield of the C—C product almost linearly decreased with decreasing copper concentrations, especially from monomer to copper ratios of 400 to 600. As the level of copper was reduced further, such linearity disappeared.

TABLE 4

|  | Ex. 2d | Ex. 2e | Ex. 2f | Ex. 2g | Ex. 2h |
| --- | --- | --- | --- | --- | --- |
| DMP | 30.0000 | 30.0000 | 30.0000 | 30.0000 | 30.0000 |
| DBEDA | 0.4300 | 0.3430 | 0.2860 | 0.2450 | 0.2150 |
| Toluene | 68.0000 | 68.0000 | 68.0000 | 68.0000 | 68.0000 |
| $Cu_2O$ | 0.0439 | 0.0351 | 0.0293 | 0.0251 | 0.0220 |
| HBr | 0.5534 | 0.4425 | 0.3687 | 0.3163 | 0.2767 |
| DDDMAC | 0.0500 | 0.0500 | 0.0500 | 0.0500 | 0.0500 |
| Total | 99.0773 | 98.8706 | 98.7340 | 98.6364 | 98.5636 |

TABLE 5

|  | mole ratio Cu:HBr | mole ratio DBEDA:Cu | mole ratio DMP:Cu | reaction time (min) | C-C yield (%) |
| --- | --- | --- | --- | --- | --- |
| Ex. 2d | 1:1 | 4.009:1 | 400:1 | 30 | 28.467 |
|  |  |  |  | 60 | 41.333 |
|  |  |  |  | 90 | 46.400 |
|  |  |  |  | 120 | 55.916 |
| Ex. 2e | 1:1 | 4.009:1 | 500:1 | 30 | 23.343 |
|  |  |  |  | 60 | 37.390 |
|  |  |  |  | 90 | 38.610 |
|  |  |  |  | 120 | 42.147 |
| Ex. 2f | 1:1 | 4.009:1 | 600:1 | 30 | 17.333 |
|  |  |  |  | 60 | 26.567 |
|  |  |  |  | 90 | 26.933 |
|  |  |  |  | 120 | 31.433 |
| Ex. 2g | 1:1 | 4.009:1 | 700:1 | 30 | 16.567 |
|  |  |  |  | 60 | 21.200 |
|  |  |  |  | 90 | 25.000 |
|  |  |  |  | 120 | 30.700 |
| Ex. 2h | 1:1 | 4.009:1 | 800:1 | 30 | 14.667 |
|  |  |  |  | 60 | 20.033 |
|  |  |  |  | 90 | 24.000 |
|  |  |  |  | 120 | 28.333 |

Also studied was the effect of the tertiary amine DMBA on C—C coupling. DMBA significantly interfered with the C—C coupling reaction under the conditions studied. The concentration of DMBA was varied from 0 to 2 weight percent with respect to the total amount of toluene used as the reaction solvent. Even when present at 0.5 weight percent, DMBA resulted in a 45% decrease in C—C coupling. At 2 weight percent, the yield of the C—C coupled products dropped by over 70% relative to the no-DMBA control.

Reaction conditions are summarized in Table 6. Held constant were a reaction temperature of 85° C., a reaction time of 90 minutes, an $O_2$ flow rate of 300 sccm, a percent solids of 30 weight percent, and a mole ratio of DBEDA to Cu of 8.15:1.

DMBA is removed from DMBA-spiked toluene as follows. 68 grams of toluene was taken in a bottle. 0.68 grams DMBA was added and shaken well. 1.2 grams of HBr (as a 48% aqueous solution), designated "HBr (1)", was then added and the bottle was capped and shaken thoroughly. Small white solid particles of DMBA/Hydrobromide were observed. The contents of the bottle were then transferred into the 250 milliliter jacketed reactor at 30° C. Stirring was continued for 15 minutes. 68 grams of water was subsequently added with stirring. The DMBA/Hydrobromide was extracted into the aqueous phase. The stirring was maintained at 150 rpm. The reactor temperature was raised to 55° C. Then, the aqueous heavy bottom phase was drained out. Subsequently, the reactor temperature was raised to 85° C. The reactions (Examples 3m, 3n, and 3o) were then carried out with the DMBA-free toluene.

Results are presented in Table 7. The purpose of these experiments is to investigate the effect on TMDQ+TMBP yield of using HBr to remove DMBA impurity in DMBA-spiked toluene (simulating recycled toluene with DMBA impurity). The results indicate the adverse effect of DMBA on TMDQ+TMBP yield. The effective removal of DMBA from toluene restores the yield of TMDQ+TMBP.

TABLE 6

|  | Ex. 2i | Ex. 2j | Ex. 2k | Ex. 2l | Ex. 2m | Ex. 2n | Ex. 2o |
|---|---|---|---|---|---|---|---|
| DMP | 30.0000 | 30.0000 | 30.0000 | 30.0000 | 30.0000 | 30.0000 | 30.0000 |
| DBEDA | 1.2000 | 1.2000 | 1.2000 | 1.2000 | 1.2000 | 1.2000 | 1.2000 |
| DMBA | 0.0000 | 0.3400 | 0.6800 | 1.3600 | 0.3400 | 0.6800 | 1.3600 |
| Toluene | 68.0000 | 68.0000 | 68.0000 | 68.0000 | 68.0000 | 68.0000 | 68.0000 |
| HBr (1) | 0.0000 | 0.0000 | 0.0000 | 0.0000 | 0.5947 | 1.1894 | 2.3788 |
| $H_2O$ | 0.0000 | 0.0000 | 0.0000 | 0.0000 | 68.0000 | 68.0000 | 68.0000 |
| $Cu_2O$ | 0.0585 | 0.0585 | 0.0585 | 0.0585 | 0.0585 | 0.0585 | 0.0585 |
| HBr (2) | 0.7374 | 0.7374 | 0.7374 | 0.7374 | 0.7374 | 0.7374 | 0.7374 |
| DDDMAC | 0.0500 | 0.0500 | 0.0500 | 0.0500 | 0.0500 | 0.0500 | 0.0500 |
| Total | 100.0459 | 100.0459 | 100.0459 | 100.0459 | 100.0459 | 100.0459 | 100.0459 |

TABLE 7

|  | mole ratio Cu:HBr | weight % DMBA in Toluene | mole ratio DMBA:Cu | Moles of HBr (DMBA removal) | mole ratio DMP:Cu | C—C yield (%) |
|---|---|---|---|---|---|---|
| Ex. 2i | 1:1 | 2 | 16.4359:1 | 0.0000 | 300.2961 | 2.2333 |
| Ex. 2j | 1:1 | 1 | 8.2179:1 | 0.0000 | 300.2961 | 13.3333 |
| Ex. 2k | 1:1 | 0.5 | 4.1089:1 | 0.0000 | 300.2961 | 17.1000 |
| Ex. 2l | 1:1 | 0 | 0:1 | 0.0000 | 300.2961 | 29.6667 |
| Ex. 2m | 1:1 | 2 | 16.4359:1* | 17.2577 | 300.2961 | 28.9000 |
| Ex. 2n | 1:1 | 1 | 8.2179:1* | 8.6289 | 300.2961 | 29.2333 |
| Ex. 2o | 1:1 | 0.5 | 4.1089:1* | 4.3144 | 300.2961 | 29.4667 |

*Initial DMBA content before HBr treatment.

Example 3

This example illustrates the synthesis of a phenylene ether oligomer having an intrinsic viscosity of 0.04-0.05 deciliter per gram and an average of at least 1.9 hydroxyl groups per molecule.

Step 1
- A. The reactor was set to 85° C. and the purge nitrogen flow was kept at 800 sccm.
- B. Over the course of about fifteen minutes, 30 grams of 2,6-dimethyl phenol (DMP) were dissolved in 48 grams toluene at room temperature, on a magnetic stirrer. The resulting solution was added to the reactor.
- C. The amines DBEDA (0.43 gram), and DDDMAC (0.05 gram) in 10 gram toluene solution were added first to the reactor. Desired amounts of $Cu_2O$ and HBr were weighed, mixed, thoroughly shaken, and then gradually added via syringe to the reactor under agitation. All weighing vessels were rinsed with the remaining 10 grams of toluene, which was added to the reactor.
- D. Once the reactor was filled and closed and a reaction mass temperature of 85° C. was attained, the oxygen flow was started at 300 sccm, and the resulting conditions were maintained for 60 to 90 minutes.

Step 2
- A. The cooling bath temperature was reduced to 30° C.
- B. DBA (0 to 1.05 gram) in 5 grams toluene solution was added to the reactor.
- C. The oxygen flow was stepwise lowered to 100 sccm or maintained at 300 sccm, depending on the reaction batch, until the end of the reaction, which was 30 to 60 minutes later. The oxygen flow was stopped at this point.

Step 3
- A. The recirculating water bath temperature was again raised to 90° C., and 0.45 grams of NTA and 5 grams of water per 100 grams of reaction mixture were added. The mixture was stirred overnight under a nitrogen purge of 50 sccm and then allowed to sit overnight at 60° C. to allow phase separation.
- B. The water phase was removed and the toluene phase was centrifuged for 30 minutes at 3000 rpm in a 23° C. thermostatted centrifuge. The light phase was then totally isolated by evaporation in a vacuum oven at 100° C. overnight.

Reaction conditions and product characterization are summarized in Table 8, where component amounts are expressed in grams. Intrinsic viscosity (IV) was determined Ubbelohde viscometer at 25° C. in chloroform. Number average molecular weight ($M_n$) was determined by gel permeation chromatography in chloroform using polystyrene standards. "Internal Biphenyl (wt %)" was determined by $^1H$ NMR and is the weight percent of

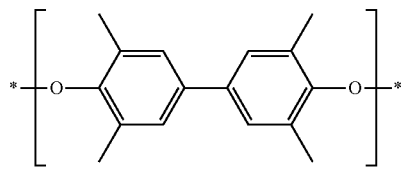

groups internal to oligomer chains, based on the total weight of oligomer. "Terminal Biphenyl (wt %)" is the weight percent of

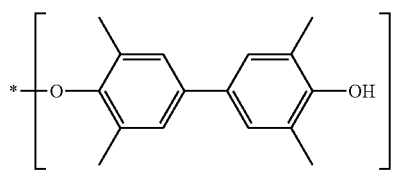

groups terminal to oligomer chains, based on the total weight of oligomer. "Incorporated C—C (wt %)" is the sum of internal and terminal biphenyl groups. "Residual TMBP (wt %)" is the weight percent of free (i.e., not incorporated into oligomer) 3,3',5,5'-tetramethyl-4,4'-dihydroxybiphenyl based on the weight of initial 2,6-dimethylphenol. "Functionality" is the average number of hydroxyl groups per oligomer molecule, determined by $^1$H NMR.

Oligomers in the intrinsic viscosity range of 0.04 to 0.06 dl/g and with an average of at least 1.92 hydroxyl groups per molecule were synthesized under the conditions listed in Table 8. Use of a monomer to copper mole ratio of 300:1, a ligand to copper mole ratio of 8.51:1, and 100 sccm oxygen flow, resulted in the bifunctional oligomers with intrinsic viscosities of around 0.04 dl/g with about 30 weight percent incorporation of tetramethyl biphenyl units along the oligomeric molecular chain. Oligomers with higher intrinsic viscosities of about 0.05 to 0.06 dl/g were obtained at a monomer to copper mole ratio of 400:1, a ligand to copper mole ratio of 4.06:1, and 300 sccm oxygen flow. Reduction in the Step 1 reaction time from 90 to 75 mins (Ex. 3b versus 3c, was associated with higher of C—O coupling in Step 2 due to less monomer consumption in Step 1. The presence of DBA, which promotes C—O coupling, was associated with very high degrees of polymerization, leading to high polymer viscosity and gel formation in Example 3c. However, running the same reaction without DBA in Step 2 resulted in better control on the C—O coupling in Step 2 as evident in Example 3d, where the DBA was not added at the beginning of Step 2 as in Ex. 3c but only after the completion of Step 2 and at the beginning of Step 3. For a given amount of C—C yield in Step 1, the intrinsic viscosity of the final oligomer post-Step 3 can also be controlled by the degree of C—O coupling in Step 2 by the level of DBA used (Ex. 3e versus 3f).

Example 4

This example compares the properties of phenylene ether oligomers prepared according to the present method with those of a copolymer of 2,6-dimethylphenol and 2,2-bis(4-hydroxy-3,5-dimethylphenyl)propane. It also compares the properties of epoxy-based materials comprising these oligomers.

Table 9 compares the properties of (Ex. 4a) a copolymer of 2,6-dimethylphenol and 2,2-bis(4-hydroxy-3,5-dimethylphenyl)propane, (Ex. 4b) a phenylene ether oligomer prepared according to the three-step embodiment of the present method, and (Ex. 4c) a phenylene ether oligomer prepared according to the two-step embodiment of the present method. The copolymer of 2,6-dimethylphenol and 2,2-bis (4-hydroxy-3,5-dimethylphenyl)propane can be prepared according to methods described in U.S. Pat. No. 7,655,278 B2 to Braidwood et al. Brookfield viscosities were measured at 25° C. at 40 or 50 weight percent oligomer in methyl ethyl ketone. Hydroxyl equivalent weight, which is the average weight of oligomer divided by the average number of hydroxyl groups per oligomer was determined by $^1$H NMR. Incorporated comonomer, which is the weight percent of comonomer residues divided by the total weight of oligomer was determined by $^1$H NMR. Glass transition temperature was determined by differential scanning calorimetry (DSC) and thermomechanical analysis (TMA). Copper content was determined according by inductively coupled plasma mass spectrometry (ICP-MS).

The results in Table 9 show that even as intrinsic viscosity is essentially constant, there can be significant variations in hydroxyl equivalent weight, and number average molecular weight due to variations in molecular weight dispersity.

TABLE 8

|  | Ex. 3a | Ex. 3b | Ex. 3c | Ex. 3d | Ex. 3e | Ex. 3f |
| --- | --- | --- | --- | --- | --- | --- |
| DMP | 30 | 30 | 30 | 30 | 30 | 30 |
| DBEDA | 1.2 | 1.2 | 1.2 | 1.2 | 0.43 | 0.43 |
| DBMA | 0.68 | 0.68 | 0.68 | 0.68 | 0.68 | 0.68 |
| Toluene | 68 | 68 | 68 | 68 | 68 | 68 |
| HBr (1)* | 1.2 | 1.2 | 1.2 | 1.2 | 1.2 | 1.2 |
| Water | 68 | 68 | 68 | 68 | 68 | 68 |
| $Cu_2O$ | 0.0585 | 0.0585 | 0.0585 | 0.0585 | 0.0439 | 0.0439 |
| HBr (2) | 0.737 | 0.737 | 0.737 | 0.737 | 0.5534 | 0.5534 |
| DBA | 1.05 | 1.05 | 1.05 | 1.05** | 1.05 | 0.5 |
| DDDMAC | 0.05 | 0.05 | 0.05 | 0.05 | 0.05 | 0.05 |
| Total | 101.0955 | 101.0955 | 101.0955 | 100.0455 | 100.1273 | 99.5773 |
| DBEBA:Cu | 8.51 | 8.51 | 8.51 | 8.51 | 4.06 | 4.06 |
| DMP:Cu | 300 | 300 | 300 | 300 | 400 | 400 |
| Step 1 rxn. time (min) | 90 | 90 | 75 | 75 | 60 | 60 |
| Step 2 rxn. time (min) | 30 | 60 | 60 | 60 | 55 | 60 |
| Step2 $O_2$ flow (sccm) | 100 | 100 | 100 | 100 | 300 | 300 |
| Step 3 rxn. time (min) | Overnight | Overnight | GELS | Overnight | Overnight | Overnight |
| IV (dl/g) | 0.043 | 0.049 | — | 0.039 | 0.062 | 0.051 |
| $M_n$ (GPC) | 641 | 624 | — | 601 | 812 | 678 |
| Incorporated C—C (wt %) | 29.29 | 30.15 | — | 29.68 | 26.91 | 30.14 |
| Internal Biphenyl (wt %) | 9.81 | 9.55 | — | 7.77 | 11.96 | 11.82 |
| Terminal Biphenyl (wt %) | 19.48 | 20.6 | — | 21.91 | 14.95 | 18.32 |
| Residual TMBP (wt %) | 8.07 | 11.82 | — | 9.86 | 4.93 | 7.05 |
| Functionality | 2 | 2 | — | 2 | 2 | 2 |

*For DMBA removal from DMBA-spiked toluene.
**DBA added at beginning of Step 3. For other examples, DBA was added after Step 1 and before Step 2.

TABLE 9

|  | Ex. 4a | Ex. 4b | Ex. 4c |
|---|---|---|---|
| IV (dl/g) | 0.087 | 0.087 | 0.088 |
| Viscosity, 50 wt % (cp) | 143 | 152 | — |
| Viscosity, 40 wt % (cp) | 23 | — | 31 |
| Functionality | 1.97 | 2.0 | 2.0 |
| Hydroxyl equivalent weight (daltons) | 816 | 568 | 393 |
| Incorporated comonomer (wt. %) | 16.18 | 21.70 | 20.72 |
| Mn (GPC) | 2000 | 1100 | 850 |
| Tg (° C.) | 137 | 116 | 108 |
| Copper (ppm) | 6.9 | 7.3 | — |

Epoxy-based materials were prepared from the oligomers above in combination with bisphenol A diglycidyl ether (CAS Reg. No. 1675-54-3, obtained as D.E.R.™ 335 from Dow Chemical), 2-Methyl-4-methyl imidazole (CAS Reg. No. 931-36-2, obtained from Acros), and methyl ethyl ketone (CAS Reg. No. 78-93-3, obtained from Fisher Scientific).

To prepare castings, D.E.R.™ 332 epoxy resin was added to a 400 milliliter Griffin beaker. The epoxy was heated on hop plate with stirring to 160° C. Once at temperature, phenylene ether oligomer (20 weight percent) was added slowly to avoid agglomerate formation. When the PPE oligomer was completely dissolved to form a homogeneous solution, the material was cooled to 110° C. and 2-methyl-4-methyl imidazole (1 part per 100 weight parts resin) was added. When the 2-methyl-4-methyl imidazole was completely dissolved, the mixture was placed in a vacuum oven set at 30 inches of mercury vacuum to remove gas from the resin. After degassing, the resin was removed from the vacuum oven and poured into a mold preheated at 120° C. The mold was then placed in the curing oven and gradually cured using the following temperature ramp: 1 hour at 120° C., 2 hours at 175° C., 2 hours at 200° C. Once the curing cycle was complete, the oven was shut off and the mold was allowed to cool overnight. The following day, the mold was taken apart, the cured part was removed and test specimens cut on a tile saw.

To prepare laminates, on a heated stir plate, phenylene ether oligomer (20 weight percent) was dissolved in methyl ethyl ketone (MEK) and heated to 50° C. Once the phenylene ether oligomer was completely dissolved, epoxy resin was added. Once the MEK, phenylene ether oligomer, and epoxy resin were completely mixed to form a homogeneous solution, the material was cooled to 30° C. and the 2-methyl-4-methylimidazole (1 part per 100 parts by weight resin) was added. Once the curing agent was dissolved, the mixture was transferred to a pan and E-Glass cloth was submerged in the resin mixture. Once properly wetted, the resulting pre-preg was air dried for 30 minutes and B-Staged for 3.0 minutes at 140° C. Two pre-pregs were layered with copper foil on the top and bottom, placed in a Teflon coated aluminum foil pouch, and cured for 3 hours at 200° C. on a PHI Laminate press.

Peel Strength Measurement. Peel strength values were determined according to IPC 2.4.8, "Peel Strength of Metallic Clad Laminates", Revision C, December 1994, except that the specimen size was 12 centimeters by 12 centimeters, instead of 5.08 centimeters by 5.08 centimeters. At least four resist strips of the width 5 millimeters were cut from the same copper clad laminate. The test strip was peeled back 5 centimeters at the tab end. The clamp was attached to the peeled back end of the test strip. The specimen was fastened with the hold down fixture so that an unencumbered vertical pull could be exerted. The end of the test strip was in a vertical position ready for testing. The tester was started and force was applied in the vertical direction at the rate of 50.8 millimeters/minute, until an 8 centimeter peel was completed. The minimum load was observed and recorded. The actual width of the test strip was measured and recorded. If the full width of the test strip did not peel, the results were discarded and another strip tested.

Peel strength, expressed in units of Newtons per millimeter, was calculated according to the formula peel strength=$LM/WS$ where LM=Minimum Load in Newtons, and WS=Measured width of peel strip in millimeters.

Dielectric Measurements. The dielectric constant, Dk, and dissipation factor, Df, of the laminates were measured after the copper foil was peeled off. A Hewlett Packard Parallel Plate RF impedance/material analyzer 1 MHz-1.8 GHz, equipped with a Hewlett Packard Dielectric Material test fixture model 16453A was used for the analysis of castings. Agilent Network Analyzer E8363B with QWED SPDRs (1.1 GHz, 1.9 GHz, 5 GHz, 10 GHz, 20 GHz) was used for the analysis of laminates. Results are presented in Table 10, where "DMP/TMBPA oligomer" is a co-oligomer of 2,6-dimethylphenol and 2,2-bis(4-hydroxy-3,5-dimethylphenyl) propane, and "DMP/TMDQ oligomer" is a co-oligomer of 2,6-dimethylphenol and 3,3',5,5'-tetramethyldiphenoquinone prepared according to the present method. In Table 10, "Dk Resin" is calculated according to the formula Dk Resin=(Dk Lam)−(Vol GF*Dk GF)/Vol Resin where "Dk Lam" is the dielectric constant of the laminate, "Vol GF" is the volume fraction of glass fibers in the laminate, "Dk GF" is the dielectric constant of the glass fibers, and "Vol Resin" is the volume fraction of resin in the laminate. Also in Table 10, "Df at 1.1 GHz" is dissipation factor at 1.1 gigahertz.

The results in Table 10 show that the dissipation factor values, Df at 1.1 GHz, of the epoxy-DMP/TMDQ oligomer laminates (0.0122, 0.0126, 0.0122) are very similar to those of the epoxy DMP/TMBPA oligomer laminates (0.0123, 0.0125, 0.0129). On the other hand, the dielectric constant values, Dk at 1.1 GHz of the laminates prepared with DMP/TMDQ oligomer (4.23, 4.12, 4.07) were higher than those of the laminates prepared with DMP/TMBPA oligomer (3.76, 3.87, 4.29). The reason can be attributed to the resin and glass contents in the laminates. The dielectric constant of E-glass is 6.0 compared to the epoxy-DMP/TMDQ oligomer resin which is 2.95 (Table 10). Therefore, the higher the amount of glass, the higher the dielectric constant. Once the dielectric constants are normalized based on resin content, the values are very similar for all the laminates.

TABLE 10

|  | DMP/TMBPA oligomer | | | DMP/TMDQ oligomer | | |
|---|---|---|---|---|---|---|
|  | Ex. 4d | Ex. 4e | Ex. 4f | Ex. 4g | Ex. 4h | Ex. 4i |
| Dk at 1.1 GHz | 3.76 | 3.87 | 4.29 | 4.23 | 4.12 | 4.07 |
| Df at 1.1 GHz | 0.0122 | 0.0126 | 0.0122 | 0.0123 | 0.0125 | 0.0129 |
| glass weight (g) | 46.12 | 48.23 | 51.92 | 58.65 | 58.25 | 55.04 |
| glass volume (mL) | 17.40 | 18.20 | 19.59 | 22.13 | 21.98 | 20.77 |
| resin weight (g) | 53.89 | 51.77 | 48.08 | 41.36 | 41.76 | 44.97 |
| resin volume (mL) | 61.16 | 58.76 | 54.57 | 46.94 | 47.39 | 51.04 |

TABLE 10-continued

|  | DMP/TMBPA oligomer | | | DMP/TMDQ oligomer | | |
| --- | --- | --- | --- | --- | --- | --- |
|  | Ex. 4d | Ex. 4e | Ex. 4f | Ex. 4g | Ex. 4h | Ex. 4i |
| Dk Resin | 3.01 | 3.05 | 3.34 | 2.98 | 2.89 | 2.99 |
| Average Dk Resin |  | 3.13 |  |  | 2.95 |  |
| Standard Deviation |  | 0.18 |  |  | 0.06 |  |

Mechanical, thermal, and chemical properties of laminates are summarized in Table 11. The peel strength, or bond, is one of the most important characteristics of the printed circuit boards. The peel strength can be defined as average load per unit width required to separate a flexible member from a rigid or another flexible member. The copper peel strength of the laminates prepared using epoxy formulations with DMP/TMBPA oligomer and with DMP/TMDQ oligomer showed very similar results, indicating a good adhesion to copper foil for all samples.

The glass transition temperature and the coefficient of thermal expansion are the most important thermal properties for the laminates used in printed circuit boards. The length of time it takes for copper-clad laminates to blister or delaminate on 288° C. molten solder is a measure of thermal resistance. Since many physical properties such as hardness, brittleness and thermal expansion undergo significant changes in the glass transition temperature region, the higher the glass transition temperature the better the performance during soldering. In addition, the effective coefficient of thermal expansion (CTE) of printed circuit boards have a great deal of influence on the reliability of solder joints in microelectronic packages. A Perkin Elmer Thermal Mechanical Analyzer was used to determine the coefficient of thermal expansion of the laminates in the z-direction. The samples were heated to 288° C. at a rate of 10° C./minute and kept at 288° C. for one hour. The Tg and CTE values of laminates prepared using DMP/TMBPA oligomer and those of laminated prepared using DMP/TMDQ oligomer were very similar.

TABLE 11

|  | DMP/TMBPA oligomer | | | DMP/TMDQ oligomer | | |
| --- | --- | --- | --- | --- | --- | --- |
|  | Ex. 4j | Ex. 4k | Ex. 4l | Ex. 4m | Ex. 4n | Ex. 4o |
| Peel strength (N/mm) | 1.85 | 1.81 | 1.69 | 1.93 | 1.94 | 1.90 |
| CTE (mm/m ° C.) above Tg | 376 | 360 | 357 | 362 | 414 | 330 |
| Tg (° C.), TMA | 196 | 197 | 202 | 200 | 193 | 199 |
| Tg (° C.), DSC | 183 | 179 | 183 | 169 | 167 | 168 |
| ash (%) | 46.11 | 48.23 | 51.92 | 58.65 | 58.25 | 55.04 |

The dielectric performance of the resins in epoxy castings was also measured. The epoxy castings were prepared by dissolving PPE oligomer (40 grams; DMP/TMBPA oligomer or DMP/TMDQ oligomer) in epoxy resin (160 grams) at 160° C. Once the PPE oligomer was completely dissolved, the material was cooled to 110° C. and catalyst (2-ethyl-4-methylimidzaole, 2 grams) was added. The mixture was then placed in a vacuum oven to remove gas from the resin. After degassing, the resin was removed from the vacuum oven and poured into a preheated mold. The mold was then placed in the curing oven and gradually cured following a temperature ramp profile ending with a maximum temperature of 200° C. The results showed a close agreement with the normalized resin Dk values from the copper clad laminates. Dk and Df values were similar for cured epoxy castings prepared with DMP/TMBPA oligomer and DMP/TMDQ oligomer.

TABLE 12

| Properties | with DMP/ TMBPA oligomer | with DMP/ TMDQ oligomer |
| --- | --- | --- |
| Dielectric constant, Dk at 1 GHz | 2.95 | 2.91 |
| Dissipation factor, Df at 1 GHz | 0.0227 | 0.0196 |

The invention claimed is:

1. A method of forming a phenylene ether oligomer, the method comprising:

reacting 2,6-dimethylphenol in the presence of toluene, oxygen, copper ion, bromide ion, and an alkylenediamine to form a first reaction mixture comprising 40 to 90 weight percent residual 2,6-dimethylphenol, and 10 to 60 weight percent 3,3',5,5'-tetramethyl-4,4'-dihydroxybiphenyl, 3,3',5,5'-tetramethyldiphenoquinone, or a combination thereof; wherein weight percent values are based on the weight of initial 2,6-dimethylphenol; and wherein the reaction of the 2,6-dimethylphenol is conducted at a mole ratio of 2,6-dimethylphenol to copper ion of 300:1 to 1000:1, at a mole ratio of alkylenediamine to copper ion of 2:1 to 8:1, in the presence of 0 to 0.2 weight percent of tertiary monoamine, based on the weight of toluene, and at a temperature of 50 to 110° C.;

reacting the residual 2,6-dimethylphenol in the presence of toluene, oxygen, copper ion, bromide ion, and alkylenediamine to form a second reaction mixture comprising 40 to 90 weight percent poly(2,6-dimethyl-1,4-phenylene ether); wherein the reacting residual 2,6-dimethylphenol is conducted at a temperature of 25 to 60° C.; and wherein any 3,3',5,5'-tetramethyl-4,4'-dihydroxybiphenyl present in the first reaction mixture is substantially converted to 3,3',5,5'-tetramethyldiphenoquinone in the second reaction mixture;

chelating the copper ion; and reacting the poly(2,6-dimethyl-1,4-phenylene ether) and the 3,3',5,5'-tetramethyldiphenoquinone to form a phenylene ether oligomer having the structure

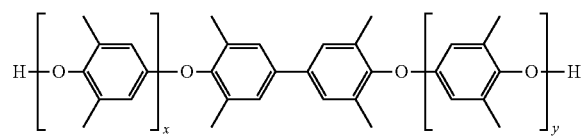

wherein x and y are independently 0 to 20, provided that the sum of x and y is at least 1 and no greater than 30; wherein the reacting the poly(2,6-dimethyl-1,4-phenylene ether) and the 3,3',5,5'-tetramethyldiphenoquinone is conducted at a temperature of 50 to 100° C.

2. The method of claim 1, wherein the alkylenediamine is selected from the group consisting of N,N'-di-($C_{1-12}$-alkyl) ethylenediamines, N,N,N'-tri-($C_{1-12}$-alkyl)ethylenediamines, N,N,N'N'-tetra-($C_{1-12}$-alkyl)ethylenediamines, N,N'-di-($C_{1-12}$-alkyl)-1,2-propylenediamines, N,N,N'-tri- (C$_{1-12}$-alkyl)-1,2-propylenediamines, N,N,N'N'-tetra-(C$_{1-12}$-alkyl)-1,2-propylenediamines, N,N'-di-(C$_{1-12}$-alkyl)-1,3-propylenediamines, N,N,N'-tri-(C$_{1-12}$-alkyl)-1,3-propylenediamines, N,N,N'N'-tetra-(C$_{1-12}$-alkyl)-1,3-propylenediamines, and combinations thereof.

3. The method of claim 1, wherein the alkylenediamine is selected from the group consisting of N,N'-di-tert-butylethylenediamine, N,N,N',N'-tetraethylethylenediamine, N,N,N',N'-tetramethylethylenediamine, N,N '-diethyl-N,N '-dimethylethylenediamine, N,N'-diethylethylenediamine, N,N'-dimethylethylenediamine, N,N,N',N'-tetramethyl-1,3-butylenediamine, and combinations thereof.

4. The method of claim 1, wherein the reaction of the 2,6-dimethylphenol is conducted at a mole ratio of 2,6-dimethylphenol to copper ion of 400:1 to 900:1.

5. The method of claim 1, wherein the reaction of the 2,6-dimethylphenol is conducted in the presence of 0 to 0.1 weight percent tertiary monoamine, based on the weight of toluene.

6. The method of claim 1, wherein the reaction of the 2,6-dimethylphenol is conducted at a mole ratio of alkylenediamine to copper ion of 3:1 to 6:1.

7. The method of claim 1, wherein the reaction of the 2,6-dimethylphenol is conducted at a temperature of 55 to 100° C.

8. The method of claim 1, wherein the reaction of the 2,6-dimethylphenol is conducted in the presence of 0 to 1 weight percent secondary monoamine, based on the weight of 2,6-dimethylphenol.

9. The method of claim 1, wherein the first reaction mixture comprises 40 to 80 weight percent residual 2,6-dimethylphenol, and 20 to 60 weight percent 3,3',5,5'-tetramethyl-4,4'-dihydroxybiphenyl, 3,3',5,5'-tetramethyldiphenoquinone, or a combination thereof, wherein weight percent values are based on the weight of initial 2,6-dimethylphenol.

10. The method of claim 1, wherein the reacting residual 2,6-dimethylphenol is conducted at a temperature of 30 to 45° C.

11. The method of claim 1, wherein the reacting the poly(2,6-dimethyl-1,4-phenylene ether) and the 3,3',5,5'-tetramethyldiphenoquinone is conducted at a temperature of 70 to 90° C.

12. The method of claim 1, wherein the reacting the 2,6-dimethylphenol and the reacting the residual 2,6-dimethylphenol are conducted in the absence of any solvent other than toluene.

13. The method of claim 1, wherein the reacting the poly(2,6-dimethyl-1,4-phenylene ether) and the 3,3',5,5'-tetramethyldiphenoquinone is conducted in the presence of the chelated copper ion.

14. The method of claim 1, wherein the sum of x and y is less than or equal to 20.

15. The method of claim 1,
wherein the alkylenediamine comprises N,N'-di-tent-butylethylenediamine;
wherein the reaction of the 2,6-dimethylphenol is conducted
at a mole ratio of 2,6-dimethylphenol to copper ion of 400:1 to 800:1,
at a mole ratio of N,N'-di-tert-butylethylenediamine to copper ion of 3:1 to 5:1,
in the presence of 0 to 0.1 weight percent secondary monoamine, based on the weight of 2,6-dimethylphenol, and
at a temperature of 70 to 90° C.;
wherein the first reaction mixture comprises 40 to 80 weight percent residual 2,6-dimethylphenol, and 20 to 60 weight percent 3,3',5,5'-tetramethyl-4,4'-dihydroxybiphenyl, 3,3',5,5'-tetramethyldiphenoquinone, or a combination thereof, based on the weight of initial 2,6-dimethylphenol;
wherein the reacting residual 2,6-dimethylphenol is conducted at a temperature of 30 to 45° C.;
wherein the reacting the poly(2,6-dimethyl-1,4-phenylene ether) and the 3,3',5,5'-tetramethyldiphenoquinone is conducted at a temperature of 70 to 90° C.; and
wherein the sum of x and y is less than or equal to 20.

\* \* \* \* \*